US00PP24623P2

(12) United States Plant Patent
Mak

(10) Patent No.: US PP24,623 P2
(45) Date of Patent: Jul. 8, 2014

(54) LILY PLANT NAMED 'TINY GLOW'

(50) Latin Name: *Lilium hybrida*
Varietal Denomination: Tiny Glow

(75) Inventor: Niels Johannes Cornelis Mak, Wieringerwerf (NL)

(73) Assignee: Mak 't Zand B.V., 't Zand (NL)

( * ) Notice: Subject to any disclaimer, the term of this patent is extended or adjusted under 35 U.S.C. 154(b) by 58 days.

(21) Appl. No.: 13/573,467

(22) Filed: Sep. 15, 2012

(51) Int. Cl.
*A01H 5/00* (2006.01)

(52) U.S. Cl.
USPC ..... Plt./315

(58) Field of Classification Search
CPC ..... A01H 5/0272
See application file for complete search history.

*Primary Examiner* — Annette Para
(74) *Attorney, Agent, or Firm* — C. A. Whealy

(57) ABSTRACT

A new and distinct cultivar of Lily plant named 'Tiny Glow', characterized by its compact and upright plant habit; vigorous growth habit; densely-foliated habit; early and freely flowering habit; upright flower buds; bright yellow-colored flowers that do not have spots; relatively drought tolerant; and good postproduction longevity.

1 Drawing Sheet

Botanical designation: *Lilium hybrida.*
Cultivar denomination: 'TINY GLOW'.

BACKGROUND OF THE INVENTION

The present Invention relates to a new and distinct cultivar of Lily plant, commercially known as Oriental Hybrid Lily, botanically known as *Lilium hybrida* and hereinafter referred to by the name 'Tiny Glow'.

The new Oriental Hybrid Lily plant is a product of a planned breeding program conducted by the Inventor in 't Zand, The Netherlands. The objective of the breeding program is to develop new potted Oriental Hybrid Lily plants with numerous large attractive flowers and good postproduction longevity.

The new Oriental Hybrid Lily plant originated from a cross-pollination in 2004 of two unnamed proprietary seedling selections of *Lilium hybrida*, not patented. The new Oriental Hybrid Lily plant was discovered and selected by the Inventor as a single flowering plant from within the resultant progeny of the stated cross-pollination in a controlled greenhouse environment in 't Zand, The Netherlands in May, 2007.

Asexual reproduction of the new Oriental Hybrid Lily plant by bulb scales in a controlled greenhouse environment in 't Zand, The Netherlands since November, 2007 has shown that the unique features of this new Oriental Hybrid Lily plant are stable and reproduced true to type in successive generations.

SUMMARY OF THE INVENTION

Plants of the new Oriental Hybrid Lily have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Tiny Glow'.

These characteristics in combination distinguish 'Tiny Glow' as a new and distinct Oriental Hybrid Lily plant:

1. Compact and upright plant habit.
2. Vigorous growth habit.
3. Densely-foliated habit.
4. Early and freely flowering habit.
5. Upright flower buds.
6. Bright yellow-colored flowers that do not have spots.
7. Relatively drought tolerant.
8. Good postproduction longevity.

Plants of the new Oriental Hybrid Lily differ primarily from plants of the female parent selection in the following characteristics:

1. Plants of the new Oriental Hybrid Lily are more compact than plants of the female parent selection.
2. Plants of the new Oriental Hybrid Lily have smaller flowers than plants of the female parent selection.
3. Plants of the new Oriental Hybrid Lily and the female parent selection differ in flower color as plants of the female parent selection have yellow-colored flowers with spots.

Plants of the new Oriental Hybrid Lily differ primarily from plants of the male parent selection in the following characteristics:

1. Plants of the new Oriental Hybrid Lily are taller than plants of the male parent selection.
2. Plants of the new Oriental Hybrid Lily have smaller flowers than plants of the male parent selection.
3. Flowers of plants of the new Oriental Hybrid Lily have narrower tepals than plants of the male parent selection.

Plants of the new Oriental Hybrid Lily can be compared to plants of Oriental Hybrid Lily 'Tiny Bee', disclosed in U.S. Plant Pat. No. 16,255. Plants of the new Oriental Hybrid Lily differ from plants of 'Tiny Bee' in the following characteristics:

1. Plants of the new Oriental Hybrid Lily and 'Tiny Bee' differ in flower bud color as plants of 'Tiny Bee' have greenish yellow-colored flower buds.

2. Plants of the new Oriental Hybrid Lily and 'Tiny Bee' differ in flower color as plants of 'Tiny Bee' have bright yellow-colored flowers with spots.

DESCRIPTION OF THE PHOTOGRAPH

The accompanying colored photograph illustrates the overall appearance of the new Oriental Hybrid Lily plant showing the colors as true as it is reasonably possible to obtain in colored reproductions of this type. Colors in the photograph may differ slightly from the color values cited in the detailed botanical description which accurately describe the colors of the new Oriental Hybrid Lily plant. The photograph comprises a side perspective view of a typical flowering plant of 'Tiny Glow' grown in a container.

DETAILED BOTANICAL DESCRIPTION

The aforementioned photograph and following observations and measurements describe plants grown during the spring in 15-cm containers in a glass-covered greenhouse in 't Zand, The Netherlands and under cultural conditions typically used in Oriental Hybrid Lily commercial production. During the production of the plants, day temperatures averaged 18° C., night temperatures averaged 15° C. and light levels averaged 6,000 lux. Measurements and numerical values represent averages for typical flowering plants. Plants were 60 days old when the photograph and description were taken. In the following description, color references are made to The Royal Horticultural Society Colour Chart, 2007 Edition, except where general terms of ordinary dictionary significance are used.

Botanical classification: *Lilium hybrida* 'Tiny Glow'.

Parentage:

*Female, or seed, parent*.—Unnamed proprietary seedling selection of *Lilium hybrida*, not patented.

*Male, or pollen, parent*.—Unnamed proprietary seedling selection of *Lilium hybrida*, not patented.

Plant description:

*Plant form and growth habit*.—Upright flowering plant; single erect flowering stem with a terminal cluster of flowers; compact and dense plant habit; vigorous growth habit.

*Plant height, soil level to top of flowers*.—About 30 cm.

*Plant diameter or spread*.—About 22 cm.

*Plant circumference*.—About 68 cm.

*Bulbs*.—Diameter: About 10 cm to 20 cm. Texture: Smooth. Color: Close to 155D.

*Flowering stems*.—Diameter: About 1 cm. Internode length: About 1.7 cm. Strength: Strong. Texture: Smooth, glabrous. Color: Close to 144B.

*Leaves*.—Arrangement and quantity: Alternate; simple; sessile; about 100 leaves develop per plant; leaves roughly horizontal. Length, upper leaves: About 14 cm. Width, upper leaves: About 1.5 cm. Length, lower leaves: About 11 cm. Width, lower leaves: About 1.2 cm. Shape: Lanceolate. Apex: Acute. Base: Acutely cuneate. Margin: Entire. Texture, upper and lower surfaces: Glabrous, smooth; leathery. Venation pattern: Parallel. Color: Developing and fully expanded leaves, upper surface: Close to 141A; venation, close to 141A. Developing and fully expanded leaves, lower surface: Close to 138A; venation, close to 138A.

Flower description:

*Flower shape and aspect*.—Flowers umbellate and funnel-shaped; when fully opened, flowers flatten and tepals recurve towards the apex; flower buds face upright and flowers face upright to outwardly.

*Flowering habit*.—Freely flowering habit, large bulbs will produce seven to nine flowers per flowering stem.

*Fragrance*.—Slightly fragrant; pleasant.

*Natural flowering season*.—Plants flower in June and July in The Netherlands; plants can be flowered year-round in the greenhouse and forced to bloom about 60 days after planting bulbs.

*Postproduction longevity*.—Good postproduction longevity, flowers last about ten to twelve days on the plant; tepals not persistent; gynoecium persistent.

*Flower buds*.—Length: About 8.5 cm. Diameter: About 2.3 cm. Circumference: About 7 cm. Shape: Lanceolate. Color: Close to 143B; color becoming closer to 9A with development; sutures, close to 143B becoming closer to 9A with development.

*Flower size*.—Diameter: About 15 cm. Length (height): About 5 cm.

*Perianth*.—Quantity and arrangement: Six tepals per flower arranged in two whorls; tepals imbricate. Tepal length, inner tepals: About 9 cm. Tepal width, inner tepals: About 4 cm. Tepal length, outer tepals: About 9.5 cm. Tepal width, outer tepals: About 3 cm. Tepal shape: Lanceolate. Tepal apex: Acute. Tepal margin: Entire; slightly undulate. Tepal texture, upper and lower surfaces: Smooth, glabrous. Tepal color: When opening and fully opened, upper surface: Close to 14A; central flair, close to 21A; at the base, close to 144A; color becoming closer to 22A with development. When opening and fully opened, lower surface: Close to 14B; color becoming closer to 22A with development.

*Pedicels*.—Length: About 4.5 cm. Diameter: About 5 mm. Angle: About 45° to 70° from vertical. Strength: Strong. Texture: Smooth, glabrous. Color: Close to 144A.

*Reproductive organs*.—Stamens: Quantity per flower: Six. Filament length: About 5.5 cm. Filament color: Close to 5D. Anther length: About 1.6 cm. Anther color: Close to 167D. Pollen color: Close to 26A. Pistils: Quantity per flower: One. Style length: About 5 cm. Style color: Between 5D and 13B. Stigma diameter: About 5 mm. Stigma shape: Lobed. Stigma color: Close to 13B; margins, close to 26A.

*Fruits*.—Length: About 1.8 cm. Diameter: About 4 mm. Color: Close to 145C.

*Seeds*.—No viable seeds have been observed on plants of the new Oriental Hybrid Lily plant.

Disease & pest resistance: Resistance to pathogens and pests common to Oriental Hybrid Lilies has not been observed on plants of the new Oriental Hybrid Lily.

Garden performance: Plants of the new Oriental Hybrid Lily have exhibited good tolerance to rain and wind and have been observed to tolerate temperatures from about −2° C. to about 40° C.

It is claimed:

1. A new and distinct Lily plant named 'Tiny Glow' as illustrated and described.

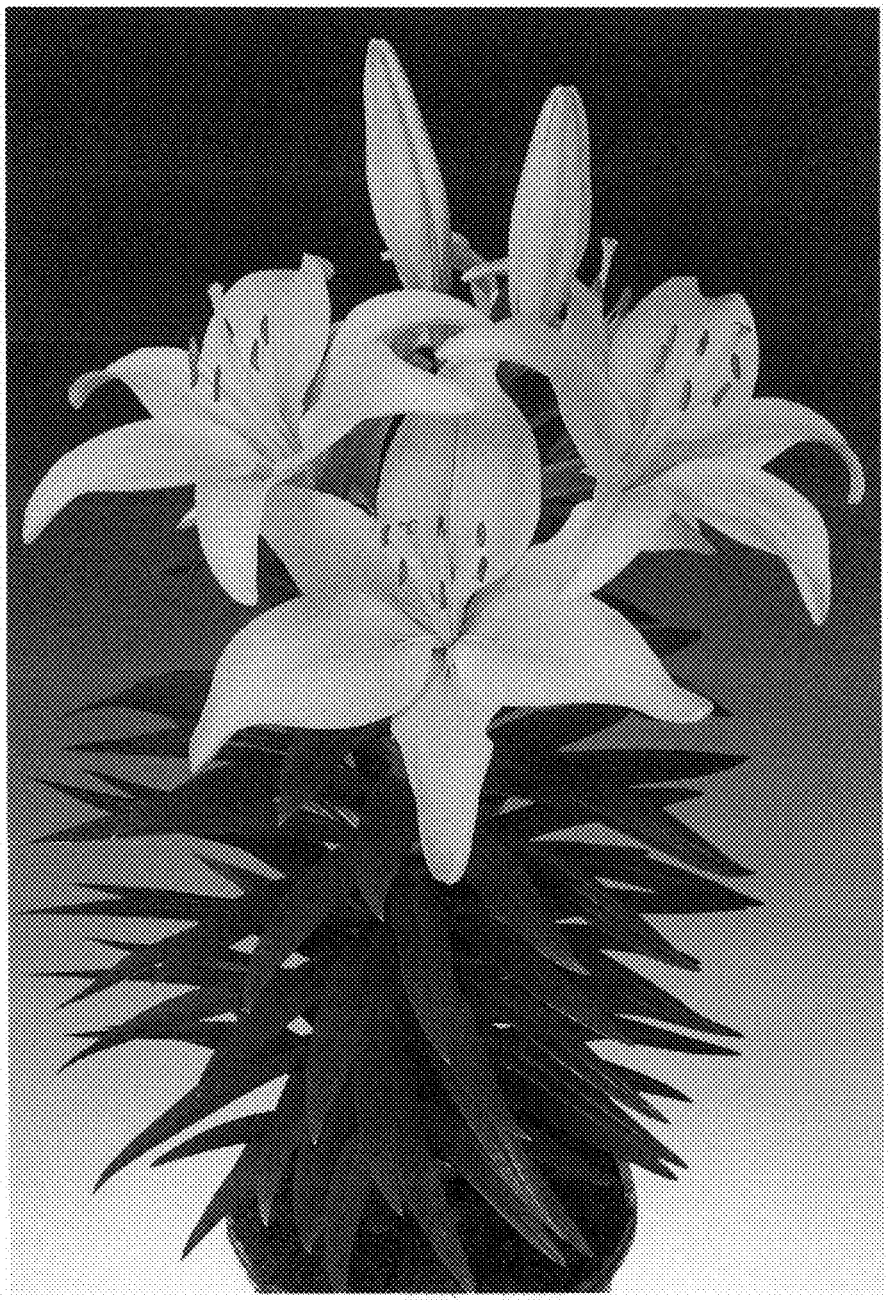

* * * * *